US00PP24531P3

(12) United States Plant Patent
Bourne

(10) Patent No.: US PP24,531 P3
(45) Date of Patent: Jun. 10, 2014

(54) GRAPEVINE NAMED 'SV 21-66-226'

(50) Latin Name: *Vitis vinifera*
Varietal Denomination: SV 21-66-226

(75) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 56 days.

(21) Appl. No.: 13/507,408

(22) Filed: Jun. 26, 2012

(65) Prior Publication Data

US 2013/0347156 P1 Dec. 26, 2013

(51) Int. Cl.
*A01H 5/00* (2006.01)

(52) U.S. Cl.
USPC ..... Plt./207

(58) Field of Classification Search
USPC ..... Plt./207
See application file for complete search history.

*Primary Examiner* — Annette Para

(74) *Attorney, Agent, or Firm* — Jondle Plant Sciences Division of Swanson & Bratschun, L.L.C.

(57) ABSTRACT

A new and distinct variety of grapevine plant named 'SV21-66-226' particularly characterized by its unusual shaped berries, very firm texture, and very large, sweet berries. Additionally, berries of the new cultivar are very responsive to applications of exogenous gibberellic acid, more than doubling in size in comparison to untreated fruit.

2 Drawing Sheets

Genus and species: *Vitis vinifera.*
Variety denomination: 'SV21-66-226'.

BACKGROUND OF THE NEW PLANT

The present invention comprises a new and distinct cultivar of grapevine botanically known as *Vitis vinifera* and hereinafter referred to as grapevine named 'SV21-66-226'. As used herein, 'grapevine' refers to all plant parts including, vines, canes, tendrils, leaves, fruit and roots of 'SV21-66-226'. Grapevine named 'SV21-66-226' is the result of an effort to produce an early ripening, green, seedless table grape with fruit characteristics superior to currently available green grape cultivar 'Thompson Seedless' (unpatented). This new cultivar originated from a cross conducted in May 2000 near McFarland, Calif. between female grapevine plant selection '13-2-138' (unpatented) and male grapevine plant 'Princess' (unpatented). Resultant ovules from the cross were harvested 42 days after pollination and cultured on 'McCown's Woody Plant Medium'. Subsequently, the resultant embryonic plants were cultured in the same medium in the laboratory under twelve hours of light from standard fluorescent lamps at 29° C. The seedlings from this effort were transplanted to the greenhouse in November of 2001 and grown in the greenhouse at 29° C. with 12 hours illumination under high pressure sodium vapor lamps. The seedling population of 118 plants was planted in the field in the spring of 2001 near McFarland, Calif. The new grapevine was selected from this seedling population in July of 2003. It was then propagated by cuttings and grafted to 'Freedom' (unpatented) rootstock in 2005. The present invention has been found to retain its distinctive characteristics through successive asexual propagations.

'SV21-66-226' has not been sold or made publically available more than one year prior to the filing date of this application.

SUMMARY OF THE INVENTION

The following are the most outstanding and distinguishing characteristics of this new variety when grown under normal horticultural practices near McFarland, Calif.:

1. Green skinned;
2. Very firm berry texture; and
3. Very large, unusual shaped berries with sweet taste.

DESCRIPTION OF THE PHOTOGRAPHS

This new grapevine is illustrated by the accompanying photographs which show fruit clusters, leaves, canes, and tendrils. The colors shown are as true as can be reasonably obtained by conventional photographic procedures. The photographs were taken from a plant about 5 years-old, grown in a field near McFarland, Calif. in 2011.

Figure 1:
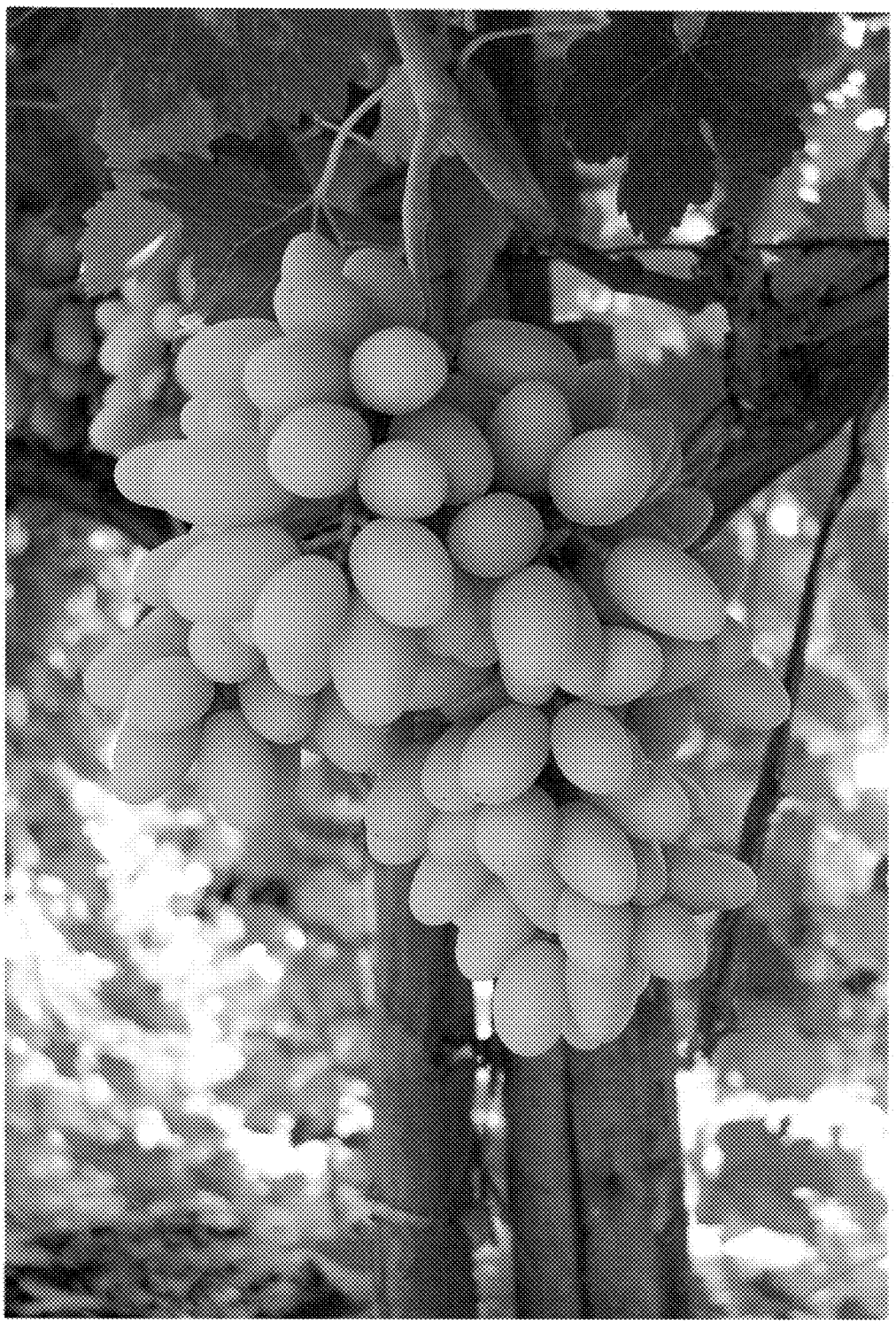

FIG. 1 Fruit clusters on the vine.

Figure 2:
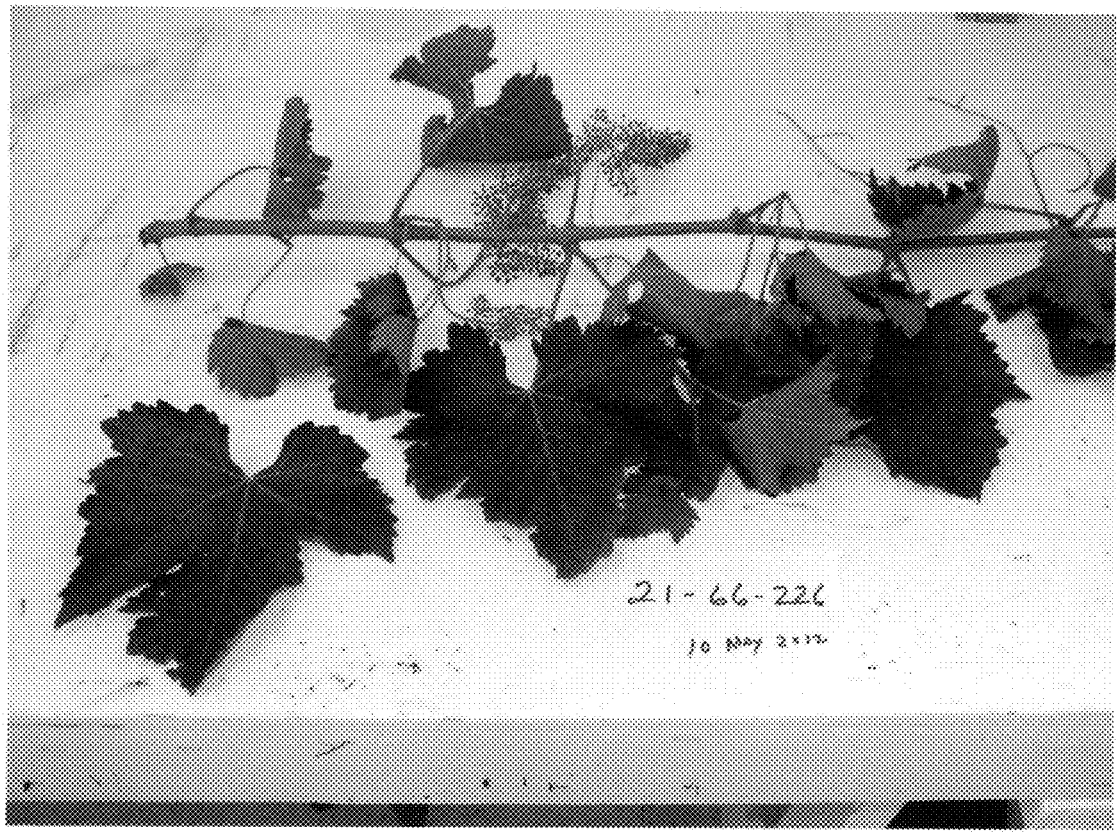

FIG. 2 Spring shoot bearing flower clusters.

DESCRIPTION OF THE NEW VARIETY

The following detailed description sets forth the distinctive characteristics of 'SV21-66-226'. Descriptions of the new invention apply to vines of 'SV21-66-226' grown on 'Freedom' rootstock at a density of 1,537 vines per hectare grown near McFarland, Calif. in 2011. These vines were in their fifth year of full production having been planted in 2006. These descriptions are believed to apply generally to the new variety grown under similar circumstances elsewhere. Color references are primarily to The Royal Horticultural Society's Colour Chart, The Royal Horticultural Society, London, United Kingdom and Munsell Color Charts for Plant Tissues by Munsell Color, 617 Little Britain Rd., New Windsor, N.Y. 12553-6148. Descriptors used herein conform to those set forth by the International Board for Plant Genetic Resources Institute Grape Descriptors (*Vitis* spp.) of 1983 and/or 1997 which were developed in collaboration with the Office Interantional de la Vigne et du Vin (OIV) and the International Union for the Protection of New Varieties of Plants (UPOV) and published in Descriptors for Grapevine (*Vitis* spp.)

(Anonymous, International Plant Genetic Resources Institute, 1997, ISBN 92-9043-352-3).

DETAILED BOTANICAL DESCRIPTION OF THE NEW PLANT

Classification:

*Family*.—Vitaceae.

*Botanical name*.—*Vitis vinifera*.

*Variety name*.—'SV21-66-226'.

Plant:

*Vigor*.—Medium; vines spur-pruned and shoot thinned to 32 shoots average 289.5 cm of growth per cane.

*Density of foliage*.—Moderate.

*Productivity*.—Very productive when spur pruned, up to 28,656 kg/hectare.

*Hardiness*.—Hardiness observed to 0° C.

*Rootstock*.—'Freedom' (unpatented).

Trunk:

*Shape*.—Broadly elliptical.

*Straps*.—Long, split.

*Surface texture*.—Shaggy.

*Trunk circumference*.—18.9 cm at 1.0 m of height.

*Inner bark color*.—RHS 174A (greyed orange group).

*Outer bark color*.—RHS 201A (grey group).

Mature leaves:

*Average blade length*.—16.8 cm.

*Average blade width*.—20.3 cm.

*Size of blade*.—Large.

*Shape*.—Pentagonal.

*Anthocyanin coloration of main veins on the upper side of the blade*.—Absent.

*Mature leaf profile*.—Cupped upwards around entire margin.

*Blistering* (*upper surface*).—Absent.

*Leaf blade tip*.—Curved upward.

*Margins*.—Lobed, serrated, undulating.

*Apex*.—Broadly acuminate.

*Bases*.—Sagittate.

*Thickness*.—Medium.

*Undulation of blade between main and lateral veins*.—Slight.

*Shape of teeth*.—Broadly conical, both sides convex.

*Length of teeth*.—7.0 mm to 10.0 mm.

*Ratio length/width of teeth*.—About 1:1.

*General shape of petiole sinus*.—Variable; open (conical) to closed.

*Tooth at petiole sinus*.—Absent.

*Petiole sinus limited by veins*.—Absent.

*Shape of upper lateral sinus*.—Closed.

*Prostrate hairs between veins* (*lower surface*).—Absent.

*Erect hairs between veins* (*lower surface*).—Absent.

*Prostrate hairs on main veins* (*lower surface*).—Absent.

*Density of erect hairs on main veins* (*lower surface*).—Sparse; found only at the base of the main veins and at junctions of smaller veins branching from the main veins.

*Prostrate hairs on main veins* (*upper surface*).—Absent.

*Upper surface*.—Summer color: RHS 135A (green group). Autumn color: RHS 12B (yellow group). Surface texture: Smooth. Surface appearance: Dull. Goffering of blade: Absent.

*Lower surface*.—Summer color: RHS 146B (yellow green group). Autumn color: RHS 12A (yellow group). Anthocyanin coloration of main veins on lower leaf surface: Absent. Glossiness: Low. Pubescence: Absent. Surface texture: Rough. Surface appearance: Dull.

*Petiole*.—Length: 16.2 cm. Length of petiole compared to middle vein: About equal. Density of prostrate hairs: Absent. Density of erect hairs: Absent. Shape of base of petiole sinus: Mostly open; outline is conical. Color: In shade: RHS N144C (yellow green group). In sun: RHS 145A (yellow green group).

Tendrils:

*Number*.—Bifurcated and trifurcated; forming at all nodes above node 5.

*Length*.—16.0 cm to 27.0 cm.

*Diameter*.—2.5 mm.

*Texture*.—Smooth.

*Color*.—RHS N144C (yellow green group).

Growing tips (young shoot):

*Pubescence*.—Abundant, prostrate.

*Color*.—RHS 144C (yellow green group).

*Anthocyanins*.—Absent.

*Shape*.—Rounded.

*Apex*.—Fully open.

*Shoot attitude*.—Semi-erect.

Woody shoot:

*Canes*.—Shape: Broadly elliptical. Internode length: About 17.9 cm. Width at node: 1.7 cm. Cross section: Circular. Surface: Smooth. Main color: RHS 165B (greyed orange group). Lenticels: Inconspicuous. Erect hairs on nodes: Absent. Erect hairs on internodes: Absent.

*Laterals*.—Shape: Broadly elliptical. Number: Laterals forming at all nodes above node 3. Length: 10.0 cm to 115.3 cm. Diameter: 3.0 mm to 8.0 mm. Internode length: 3.1 cm to 8.3 cm. Color: RHS 144A (green group).

*Buds*.—Shape: Slightly pointed. Cane bud fruitfulness: Basal buds fruitful, usually 2 clusters per shoot. Length: 4.1 mm. Width: 3.7 mm. Height: 4.9 mm. Color: RHS 165A (greyed orange group). Texture: Smooth.

Flowers:

*Flower sex*.—Perfect.

*Position of first flowering nodes*.—Third or fourth node.

*Number of inflorescences per shoot*.—Usually 2.

*Calyptra color*.—RHS 141C (green group).

*Ovary length*.—3.0 mm.

*Ovary width*.—1.5 mm.

*Ovary color*.—RHS 134A (green group).

*Filament length*.—2.0 mm.

*Filament color*.—Translucent, absence of pigmentation.

*Anther length*.—1.0 mm.

*Anther color*.—RHS 8C (yellow group).

*Date of full bloom*.—May 8.

Fruit:

*Ripening period*.—Early mid-season, about 10 days before 'Thompson Seedless' at Delano, Calif.

*Date of ripening*.—August 9 in McFarland, Calif.

*Use*.—Fresh market.

*Keeping quality*.—Very good.

*Shipping quality*.—Good, some clusters have few berries with slight bruising.

*Date of first harvest*.—August 9.

*Solids-sugar*.—High, about 20 brix at full maturity.

*Refractometer test*.—19.0 brix.

*Cluster.*—

*Bunch.*—Size: Medium. Length (peduncle excluded): About 18.8 cm. Width: About 11.2 cm. Weight: Natural, without gibberellic acid treatment: 672.0 g. With gibberellic acid treatment: 782.0 g. Density: Well-filled, but loose. Number of berries: 134. Form: Conical.

*Peduncle.*—Length: About 28.2 cm. Lignification: Medium. Color: RHS N144C (yellow green group).

*Berry.*—Size: Large. Uniformity of size: Uniform. Weight: Natural, without gibberellic acid treatment: 4.1 g. With gibberellic acid treatment: 9.5 g. Shape: Natural, without gibberellic acid treatment: Ovate. With gibberellic acid treatment: Ovate. Presence of seeds: Seedless; most berries develop one or two small, soft rudimentary seeds less than 1.0 mm in length. Cross section: Circular. Dimensions: Longitudinal axis: About 2.5 cm at base. Horizontal axis: About 2.1 cm. Skin color (without bloom): RHS 144C (yellow green group). Coloration of flesh: Translucent; RHS 150B (yellow green group). Juiciness of flesh: Very juicy. Berry firmness: Very firm. Particular flavor: Neutral, typical vinifera. Bloom (cuticular wax): Weak. Pedicel length: 1.0 cm. Berry separation from pedicel: With difficulty.

*Skin.*—Thickness: Medium. Texture: Tender. Reticulation: Absent. Roughness: Absent. Tenacity: Tenacious to flesh. Tendency to crack: Resistant.

COMPARISON WITH PARENTAL AND COMMERCIAL VARIETIES

Grapevine named 'SV21-66-226' differs form the female parent grapevine '13-2-138' (unpatented) in that 'SV21-66-226' has ovate shaped, seedless berries and flowers with functional pollen, whereas '13-2-138' has spherical shaped berries with partially lignified seed traces and flowers that are pistillate.

Grapevine named 'SV21-66-226' differs from its male parent, 'Princess' (unpatented) in that 'SV21-66-226' has ovate shaped, bright green berries that do not brown internally while in cold storage, whereas 'Princess' has oblong shaped, yellow berries and berries that brown internally while in cold storage.

Grapevine named 'SV21-66-226' differs from the commercial cultivar 'Thompson Seedless' in that 'SV21-66-226' has ovate shaped, bright green berries, whereas 'Thompson Seedless' has elongate shaped, light green berries. The berries of 'SV21-66-226' have a superior eating quality and larger berries at harvest after standard vineyard practices of application of exogenous gibberellic acid and girdling of the vine trunks as compared to 'Thompson Seedless'. Additionally, 'SV21-66-226' has fruitful shoots with spur pruning to two buds, whereas 'Thompson Seedless' lacks fruitfulness with spur pruning.

'SV21-66-226' is most similar to its sibling from the same population, grapevine named '21-66-158' (U.S. Plant patent application Ser. No. 13/507,417), from which it can be distinguished by lower fruitfulness (1 cluster on most shoots versus 2 clusters on most shoots of '21-66-158') and an ovate berry shape versus the oblong berry shape of '21-66-158'.

I claim:

1. A new and distinct variety of grapevine plant named 'SV21-66-226', shown and described herein.

* * * * *